United States Patent
Gupton et al.

(10) Patent No.: US 11,059,788 B2
(45) Date of Patent: Jul. 13, 2021

(54) STREAMLINED SYNTHESES OF FLUOROQUINOLONES

(71) Applicant: VIRGINIA COMMONWEALTH UNIVERSITY, Richmond, VA (US)

(72) Inventors: Frank B. Gupton, Midlothian, VA (US); Perrer N. Tosso, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/621,992

(22) PCT Filed: Jun. 12, 2018

(86) PCT No.: PCT/US2018/036991
§ 371 (c)(1),
(2) Date: Dec. 12, 2019

(87) PCT Pub. No.: WO2018/231747
PCT Pub. Date: Dec. 20, 2018

(65) Prior Publication Data
US 2020/0123111 A1    Apr. 23, 2020

Related U.S. Application Data

(60) Provisional application No. 62/518,264, filed on Jun. 12, 2017.

(51) Int. Cl.
*C07D 403/04* (2006.01)
*C07D 215/56* (2006.01)
*C07C 227/16* (2006.01)
*C07C 229/34* (2006.01)

(52) U.S. Cl.
CPC .......... *C07D 215/56* (2013.01); *C07C 227/16* (2013.01); *C07D 403/04* (2013.01); *C07C 229/34* (2013.01)

(58) Field of Classification Search
CPC ..................................................... C07D 403/04
USPC ............................................................ 544/363
See application file for complete search history.

(56) References Cited

U.S. PATENT DOCUMENTS

| 5,051,418 A | 9/1991 | Schriewer et al. |
| 5,639,886 A | 6/1997 | Zerbes et al. |
| 5,703,231 A * | 12/1997 | Randall ................ C07D 463/12 540/200 |

FOREIGN PATENT DOCUMENTS

| EP | 1 160 241 A3 | 8/2002 |
| WO | 2001/085692 A2 | 11/2001 |

OTHER PUBLICATIONS

Lin, H. et al.: A rapid total synthesis of ciprofloxacin hydrochloride in continuous flow. Angew. Chemie, Int. Ed., vol. 56(30), pp. 8870-8873, 2017.*
Benneville et al, "Reaction of beta-Alkoxyacrylic Esters with Secondary Amines", J. Am. Chem. Soc. 1950, vol. 72, No. 8, pp. 3725-3726.
Schwalbe et al. "Synthesis of a Library of Ciprofloxacin Analogues by Means of Sequential Organic Synthesis in Microreactors", QSAR & Combinatorial Science, 2005, vol. 24, Issue 6, pp. 758-768.
Amii et al., "Flow microreactor synthesis in organo-fluorine chemistry", Beilstein J. Org. Chem. 2013, vol. 9, pp. 2793-2802.
Lin et al: "A Rapid Total Synthesis of Ciprofloxacin Hydrochloride in Continuous Flow", Angewandte Chem, vol. 56 pp. 8870-8873, 2017.

* cited by examiner

*Primary Examiner* — Charanjit Aulakh
(74) *Attorney, Agent, or Firm* — W & C IP

(57) ABSTRACT

Methods of synthesizing fluoroquinolones such as ciprofloxacin are provided. The methods utilize affordable materials, reduce the number of synthesis steps and provide high yields.

5 Claims, No Drawings

STREAMLINED SYNTHESES OF FLUOROQUINOLONES

STATEMENT OF FEDERALLY SPONSORED RESEARCH AND DEVELOPMENT

This invention was made with government support under 547747 awarded by the Defense Advanced Research Projects Agency (DARPA). The United States government has certain rights in the invention.

BACKGROUND OF THE INVENTION

Field of the Invention

The invention generally relates to improved methods of synthesizing fluoroquinolones such as ciprofloxacin. In particular, the invention provides synthesis routes that utilize affordable materials, reduce the number of synthesis steps and provide high yields.

Description of Related Art

Ciprofloxacin is a second-generation fluoroquinolone broad spectrum antibiotic. It is used to treat a number of bacterial infections, including bone and joint infections, intra-abdominal infections, certain types of infectious diarrhea, respiratory tract infections, skin infections, typhoid fever, and urinary tract infections, among others. The drug can be taken by mouth (in solid or liquid form), in eye drops, or intravenously.

Ciprofloxacin is on the World Health Organization's List of Essential Medicines, the most effective and safe medicines needed in a health system. However, since its original discovery by Bayer AG, little effort has been made to improve the batch synthesis of ciprofloxacin, even though the initial patent has expired.

There is an ongoing need for improved methods of synthesizing fluoroquinolones, e.g. improved with respect to the time required for synthesis, the yield and cost. In particular, there is need to develop a high yield streamlined synthesis that can be readily translated into a continuous manufacturing platform.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

In some aspects, what is provided is methods of synthesizing fluoroquinolone antibiotics such as ciprofloxacin. The disclosed syntheses significantly improve current processes by reducing the number of steps to two or three high yielding steps.

In addition, methods of producing enamines (such as synthon 3) from vinyl ethers are provided.

In addition, exemplary continuous flow processes are provided which require fewer reactors and unit operations compared to the prior art.

It is an object of this invention to provide a method of forming an enamine from a vinyl ether, comprising reacting the vinyl ether with a substituted amine. In some aspects, the vinyl ether is

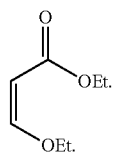

In some aspects, the substituted amine is

wherein $R_3$ is: a C1-C12 alkyl chain, which may be branched or unbranched, substituted or unsubstituted and saturated or unsaturated; or a unicyclic, bicyclic or tricyclic ring comprising 3-12 carbon atoms, which may be substituted or unsubstituted and saturated or unsaturated; or a unicyclic or bicyclic heterocyclic ring comprising 3-12 carbon atoms and having one or more ring atoms that is N, S, or O.

In additional aspects, the substituted amine is

In other aspects, the conditions suitable for forming the product include one or more of: conducting the step of reacting at a temperature in the range of from 60 to 180° C.; conducting the step of reacting at a pressure of atmosphere to 40 PSI; and conducting the step of reacting in at least one suitable solvent selected from the group consisting of toluene, tetrahydrofuran (TFH), methyl-tetrahydrofuran, dimethyl sulfoxide (DMSO), dimethylformamide (DMF), N-methyl-2-pyrrolidine (NMP) and acetonitrile (ACN) or neat. In further aspects, the step of reacting is conducted in DMSO at 130° C. and 25 PSI. In yet further aspects, the method is conducted using a microwave, a batch system or a flow system.

Also provided is a method of synthesizing a fluoroquinolone, comprising
i) reacting

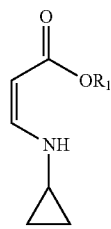

where $R_1$ is H or C1-C12 branched or unbranched alkyl, or cyclic or heterocyclic, and may be substituted or unsubstituted and saturated or unsaturated, with

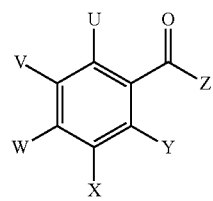

wherein U, V, W, X, and Y are the same or different and are H or halogen, alkyl, alkoxy or a peptide coupling group; and Z is a halogen or a peptide coupling group;

to form:

Intermediate (B)

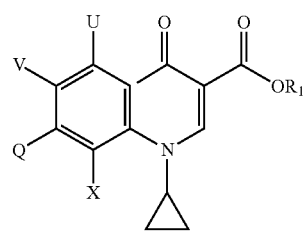

or

Intermediate A

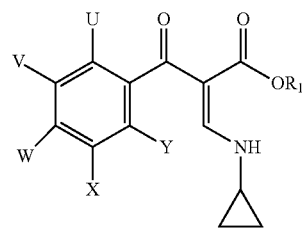

wherein if Intermediate A is formed, the method further comprises a step of ring closure to form Intermediate B or Intermediate C

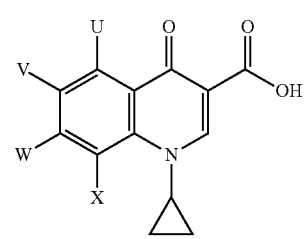

and

I. ii) reacting Intermediate B with a compound Q, which comprises a reactive amine, to yield

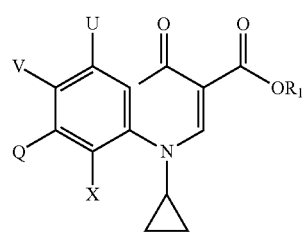

and iii) reacting BQ with a base to form the fluoroquinolone;

or

II. iv) reacting Intermediate C with a compound Q, which comprises a reactive amine to form the fluoroquinolone.

In some aspects, the peptide coupling functional group is a carboxylic acid, a carboxylate salt, or a carboxylic ester. In further aspects, the halogen is Br, Cl or F. In yet further aspects, U and X are H; V, W and Y are F; Z is Cl; Q is piperazine; and the fluoroquinolone is ciprofloxacin. In additional aspects, one or more of steps i)-iii) is performed using a microwave, a batch system or a flow reactor.

Also provided is a method of synthesizing ciprofloxacin, comprising i) reacting

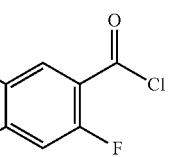

with

to form

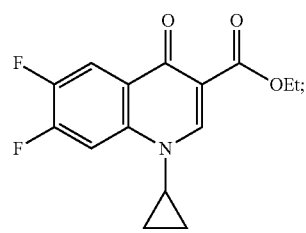

ii) reacting

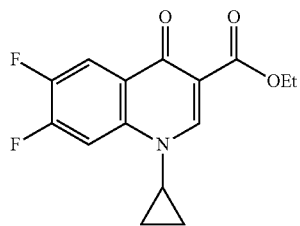 [SMILES: CCOC(=O)c1cn(C2CC2)c2cc(F)c(F)cc2c1=O]

with

to form

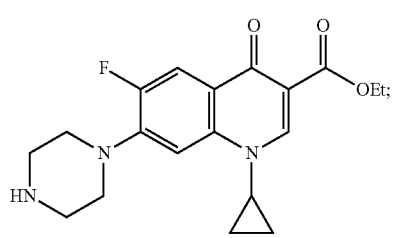 [SMILES: CCOC(=O)c1cn(C2CC2)c2cc(N3CCNCC3)c(F)cc2c1=O]

and
iii) reacting

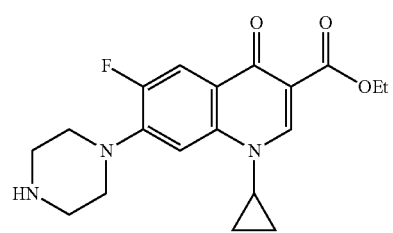

with a base to form ciprofloxacin:

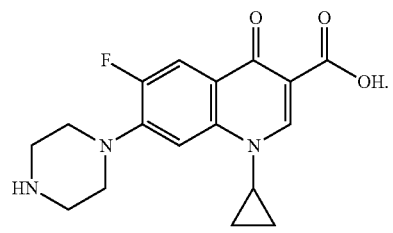

In some aspects, one or more of steps i)-iii) is performed using a microwave, a batch system or a flow reactor. In additional aspects, one or more of steps i)-iii) is performed in a flow reactor. In further aspects, steps i)-iii) include:

i) in a first flow reactor, reacting

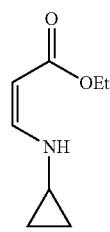

with

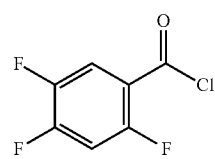

at ambient temperature to yield

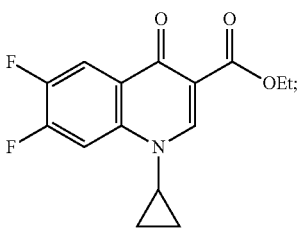

ii) in a second flow reactor, reacting the

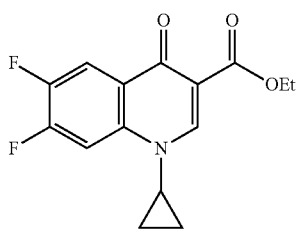 [SMILES: CCOC(=O)c1cn(C2CC2)c2cc(F)c(F)cc2c1=O]

with piperazine

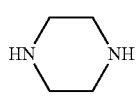

in the presence of dimethylsulfoxide (DMSO) and at a temperature in the range of 40° C. to 180° C. to yield

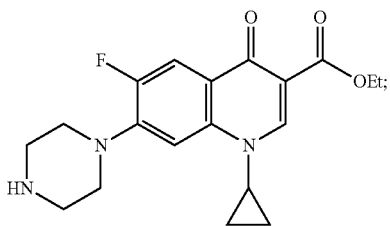

and
iii) in a third flow reactor, reacting the

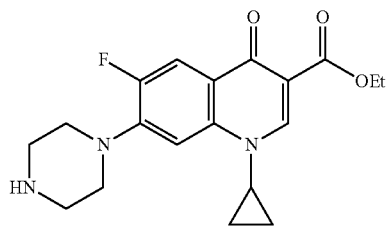

with a base, under pressure, to yield ciprofloxacin:

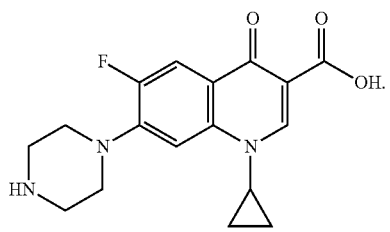

In some aspects, the pressure in the third reactor is from 30 to 150 PSI. In other aspects, the base is 1.0 M NaOH. In yet further aspects,

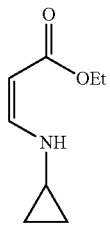 [SMILES: CCOC(=O)/C=C\NC1CC1]

is formed by reacting

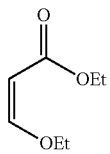

with

DETAILED DESCRIPTION

The present disclosure provides methods for synthesizing fluoroquinolones, e.g. fluoroquinolone antibiotics.

Definitions

ACN: acetonitrile
DBU: 1,8-Diazabicyclo[5.4.0]undec-7-ene
DMF: dimethylformamide
DMSO: dimethyl sulfoxide
LDA: Lithium diisopropylamide
$Li_2$: Lithium
$Li_2O$: Lithium oxide
LiH: Lithium Hydride
LiHMDS: lithium bis(trimethylsilyl)amide is a lithiated organosilicon compound with the formula $LiN(SiMe_3)_2$
NMP: N-methyl-2-pyrrolidine
THF: tetrahydrofuran Reactor: Those of skill in the art will recognize that many types of reactors for conducting chemical reactions are known. The most common basic types of chemical reactors are tanks (e.g. where the reactants mix in the whole volume) and pipes or tubes (e.g. for laminar flow reactors and plug flow reactors). Both types can be used as continuous reactors or batch reactors, and either may accommodate one or more solids (reagents, catalysts, or inert materials). The reagents and products may be fluids (liquids or gases). Reactors in continuous processes are typically run at steady-state, whereas reactors in batch processes are necessarily operated in a transient state. Examples of chemical reactors include batch reactors, continuous stirred-tank reactors (CSTR), plug flow reactors (PFR), spinning disk reactors (SDR), spinning tube-in-tube reactors (STT) and combinations of these.

In some aspects, the fluoroquinolone antibiotic is ciprofloxacin:

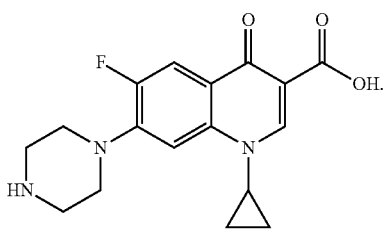

In some aspects, the fluoroquinolone syntheses start with the enamine synthon (3) (ethyl(Z)-3-(cyclopropylamino) acrylate):

Synthon (3)

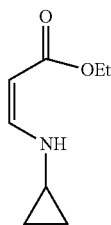

In addition, in some exemplary aspects, enamine synthon (3) is advantageously prepared from the affordable starting materials ethyl 3-ethoxyacrylate (2) and cyclopropylamine:

2

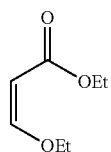

by way of a novel reaction for forming enamines from vinyl ethers, as follows:

Reaction A

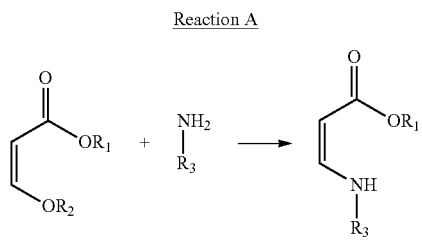

wherein R1, R2 and R3 are: a C1-C12 alkyl chain, which may be branched or unbranched, substituted or unsubstituted and saturated or unsaturated; or may be unicyclic, bicyclic or tricyclic, comprising 3-12 carbon atoms in each ring; and may be substituted (e.g. by C=O, NH, C1-C10 alkyl, etc.) or unsubstituted, and saturated or unsaturated; or heterocyclic (uni-, bi- or tricyclic) comprising 3-12 carbon atoms per ring and one or more heterologous ring atoms such as N, S, O, etc. The reaction is carried out at suitable temperatures such as e.g. in a temperature range of from about 30 to 180° C., such as 30, 40, 50, 60, 70, 80, 90, 100, 110, 120, 130, 140, 150, 160, 170 or 180° C., e.g. at 130° C. The reaction may be conducted under pressure, e.g. at about atmosphere to 40 PSI, such as 5, 10, 15, 20, 25, 30, 35 or 40 PSI, usually at about 25 PSI. The reaction is performed in at least one suitable solvent, examples of which include but are not limited to: THF, toluene, DMSO, DMF, NMP, ACN. In some aspects, the solvent is DMSO. Those of skill in the art will recognize that the reactions described herein may be conducted using or incorporated into any known reaction strategy, including but not limited to batch syntheses of one or more steps of a reaction, syntheses that utilize a microwave for one or more steps of a reaction, flow syntheses (e.g. that utilize multiple reactors), etc.

In some aspects, R3 is cyclopropyl, propyl, benzyl or cyclohexyl. In particular, for the synthesis of Synthon (3), RI and R2 are ethyl, R3 is cyclopropyl and Synthon (3) is produced via a reaction that allows early insertion of cyclopropylamine e.g. during ciprofloxacin synthesis, as follows:

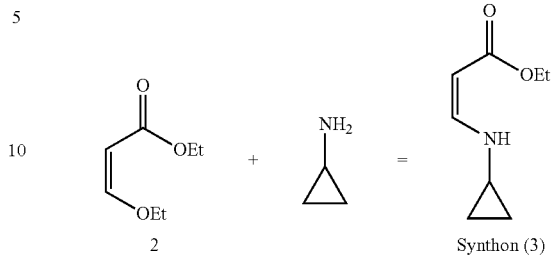

Synthon (3)

However, Synthon (3) from other sources or made with other reactions may also be employed in the reactions described herein, e.g. from commercial sources, or produced by alternative reactions such as the addition of ethyl propiolate to cyclopropyl amine as shown below (see reference 16)

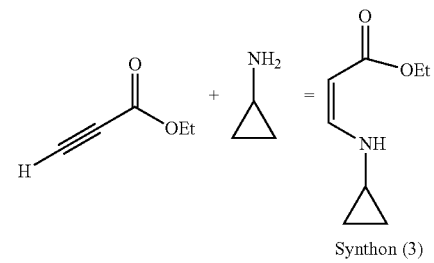

Synthon (3)

A generic synthesis route for fluoroquinolones is as follows:

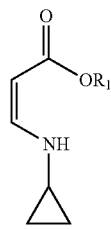

(in which R1 is as listed for Reaction A above) is reacted with a compound having generic Formula 20

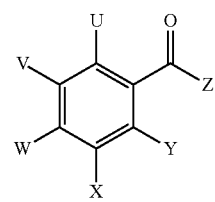

where U, V, W, X, Y are the same or different and are H, halogen, such as Br, F or Cl; and Z is a halogen such as Br, F or Cl; or U, V, W, X, Y may be alkyl or alkoxy groups. Alternatively, U, V, W, X, Y and Z may be substituents on other chemical groups such another peptide coupling reagent (e.g. such a carboxylic acid, a carboxylate salt, carboxylic esters, etc.).

This reaction results in the production of, for example, generic intermediate A or B:

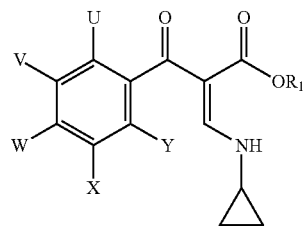

A

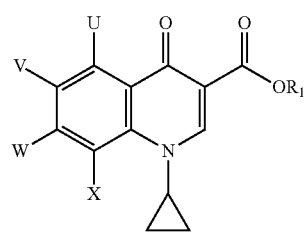

B

Under some reaction conditions, Intermediate A is formed and a separate step of ring closure is required, e.g. see ciprofloxacin Synthesis Routes 1 and 2 below. However, under other reaction conditions, a separate step of ring closure is not required, e.g. see ciprofloxacin Synthesis Routes 3-5 below. In other words, in some aspects, the reaction includes steps of forming Intermediate A and then reacting Intermediate A to effect ring closure and form Intermediate B. If needed, ring closure can be performed, e.g. by heating Intermediate A to a high temperature (e.g. about 100° C.) in a suitable solvent (e.g. THF, toluene, DMSO, DMF, NMP or ACN, preferably DMSO) in the presence of a suitable reactant such as DBU or LiOH, to facilitate ring closure.

Intermediate B is then reacted with a compound Q that comprises a reactive amine group, resulting in the replacement of W by the radical of Q, to yield:

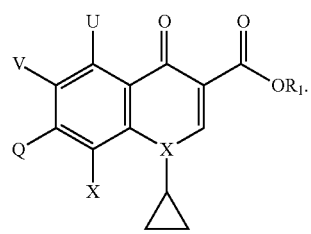

(BQ)

BQ can be further reacted with a base to convert the $OR_1$ group to OH, thereby yielding a fluoroquinolone. Additional reactions (e.g. conversion to a salt form, etc.) can be performed as needed.

However, in some aspects, such as in Synthesis Route 2 below, the step of ring closure also affords conversion of OEt to OH so that, in contrast the other synthetic routes, an "OH" containing intermediate, Intermediate C, is formed:

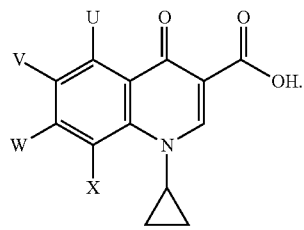

Intermediate C reacts with the compound comprising an amine function (Q herein), thereby forming the final product directly, without the need of further exposure to a base. The final product may be represented as:

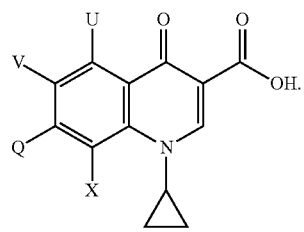

According to some aspects, when ciprofloxacin is synthesized, chemoselective C-acylation of the enamine synthon is achieved at a high yield affording the exemplary intermediate (5):

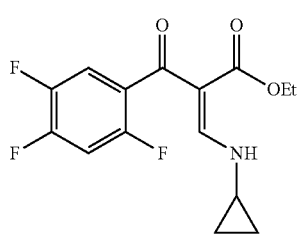

5 and/or in some aspects, the intermediate (6):

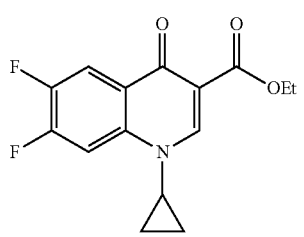

6 and/or the intermediate (7):

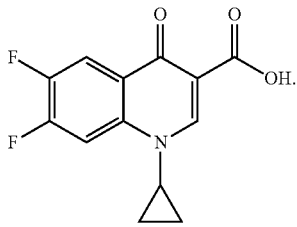

Exemplary synthesis routes for ciprofloxacin include Synthesis Routes 1-5, described in detail below.

Exemplary Ciprofloxicin Synthesis Route 1

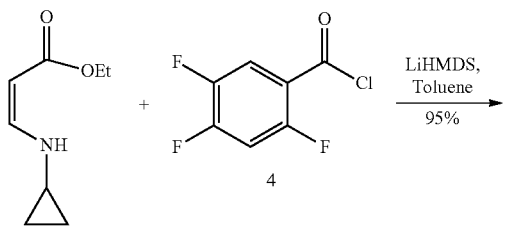

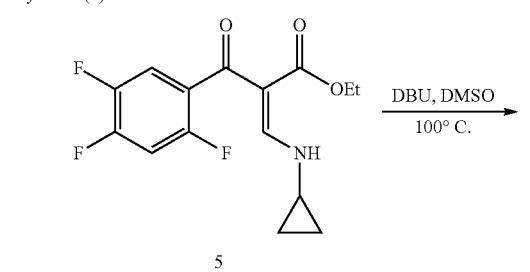

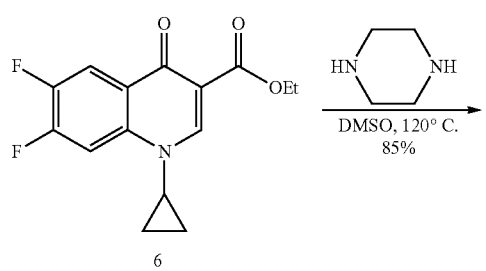

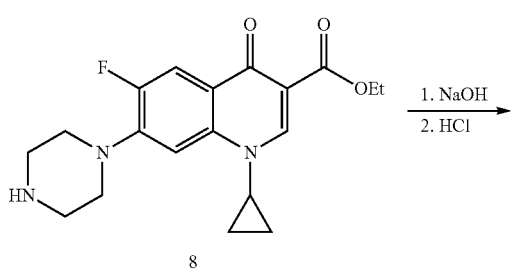

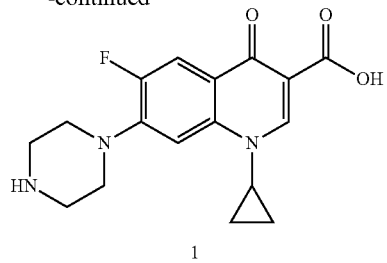

As depicted, Synthesis Route 1 comprises four reaction steps, the first of which is the production of synthon (3), as follows:

Reaction I

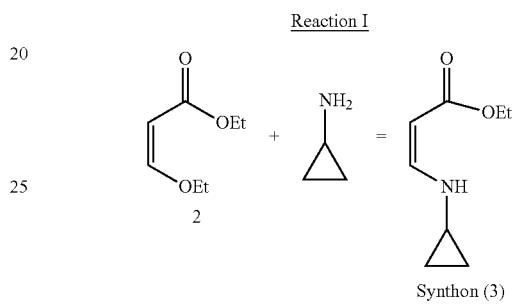

The reaction is performed within a temperature range of from about 60 to about 180° C., such as about 30 to 180° C. such as 30, 40, 50, 60, 70, 80, 90, 100, 110, 120, 130, 140, 150, 160, 170 or 180° C., e.g. at 130° C. The reaction is generally also performed under pressure, atmosphere to 40 PSI, such as 5, 10, 15, 20, 25, 30, 35 or 40 PSI, usually at about 25 PSI. In addition, Reaction I is generally performed in a solvent that dissolves both polar and nonpolar compounds, examples of which include such as dimethyl sulfoxide (DMSO), dimethylformamide (DMF), N-Methyl-2-pyrrolidone (NMP) and acetonitrile (ACN). In some aspects, the solvent is DMSO.

The reaction is generally complete after about 2-6 (e.g. about 4) hours.

Synthon 3 is then reacted with a compound having generic Formula 20

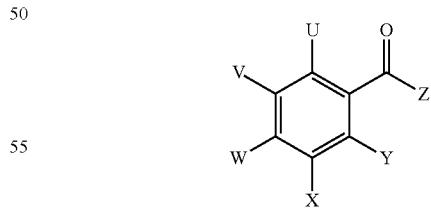

where U, V, W, X, Y are the same or different and are halogen, such as Br, F or Cl and Z is a halogen such as Br, F or Cl or, U, V, W, X, Y may be alkyl or alkoxy groups. Alternatively, U, V, W, X, Y and Z may be other chemical groups such another peptide coupling reagent (e.g. such a carboxylic acid, a carboxylate salt, carboxylic esters, etc.)

In Synthesis Route 1, the compound is compound 4 (2,4,5-trifluorobenzoyl chloride):

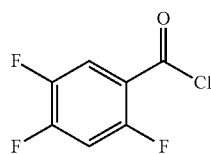

and the reaction is performed under the following conditions to afford intermediate 5: at 0° C. in suitable solvents such as but not limited to toluene (PhMe) or tetrahyfuran (THF) in the presence of LiHMDS (1.1 equiv.) in a ratio of 1:1.1 (3:4); for a period of time ranging from about 30 mins to about 1 h. Reactant 4 is readily available from commercial sources.

In an exemplary synthesis, to 250 mL dried round bottom flask 3 (1 g, 6.45 mmoles) was added in toluene (18 mL) under argon. The mixture was cooled to 0° C. and lithium bis(trimethylsilyl)amide (7.01 mL, 7.01 mmoles) was added and the resulting bright yellow solution was stirred for 30 mins followed by the dropwise addition of 4 (2,4,5-trifluorobenzoyl chloride) (1.36 g, 7.01 mmoles). The mixture was allowed to warm to room temperature and stirred (e.g. for about 1 h and then diluted with a suitable solvent such as CH$_2$Cl$_2$, followed by the quenching (e.g. using 10 mL saturated aqueous NH$_4$Cl. The organic layer is then washed (e.g. with brine) and dried using a suitable agent (e.g. over Na$_2$SO$_4$). The organic solvent may be removed under pressure. The crude is purified using a suitable technique (e.g. flash chromatography on a silica gel column) using a suitable eluent (e.g. a mixture of hexanes/EtOAc) to afford the final product (e.g. as a yellow oil in suitable quantities. In some aspects, a yield greater than 90% is achieved, e.g. in quantitative yield, such as 2.14 mg, or 96%. Lithiation of the enamine assists in the chemoselective acylation of 3. LDA, n-BuLi, t-BuOLi, LiH, and L$_2$ can also be used as the enamine lithiating agent. THF and PhMe are preferred solvents for this transformation.

Ring closure of intermediate 5

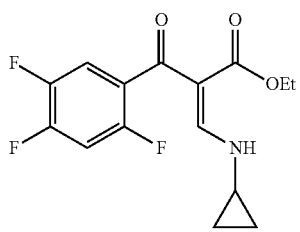

to yield intermediate 6

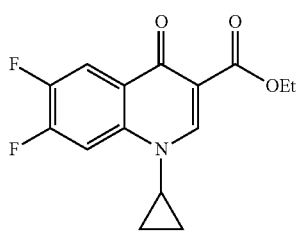

is effected by reaction in a temperature range of from about 40 to about 180° C., e.g. at about 40, 50, 60, 70, 80, 90, 95, 100, 110, 120, 130, 140, 150, 160, 170, 180 or 105° C., such as at 100° C. In some aspects, the reaction conditions include the use of DBU or K$_2$CO$_3$ or NaH as a base in the in the S$_N$Ar reaction and DMSO, DMF, NMP or ACN as solvents or solvent combinations.

In some aspects, intermediate 6 is then converted to the final product, ciprofloxacin (1), by reaction with the base piperazine at a temperature in the range of from about 50° C.–180° C. for about 2 h (e.g. about 90, 100, 110 or 120° C. for about 0.5, 1, 1.5, 2.0, 2.5 or 3.0 hours). Upon completion of the nucleophilic substitution reaction, the ester is hydrolyzed by adding a base (e.g. 1M NaOH) to the reaction mixture. A pH adjustment of the reaction mixture to pH 7 (e.g. with 4N HCl) ensues and the mixture is cooled (e.g. at 4° C. in the fridge) to allow the product to precipitate. The precipitate is then filtered and washed e.g. with water and acetone to afford the product, ciprofloxacin (1).

Exemplary Ciprofloxacin Synthesis Route 2

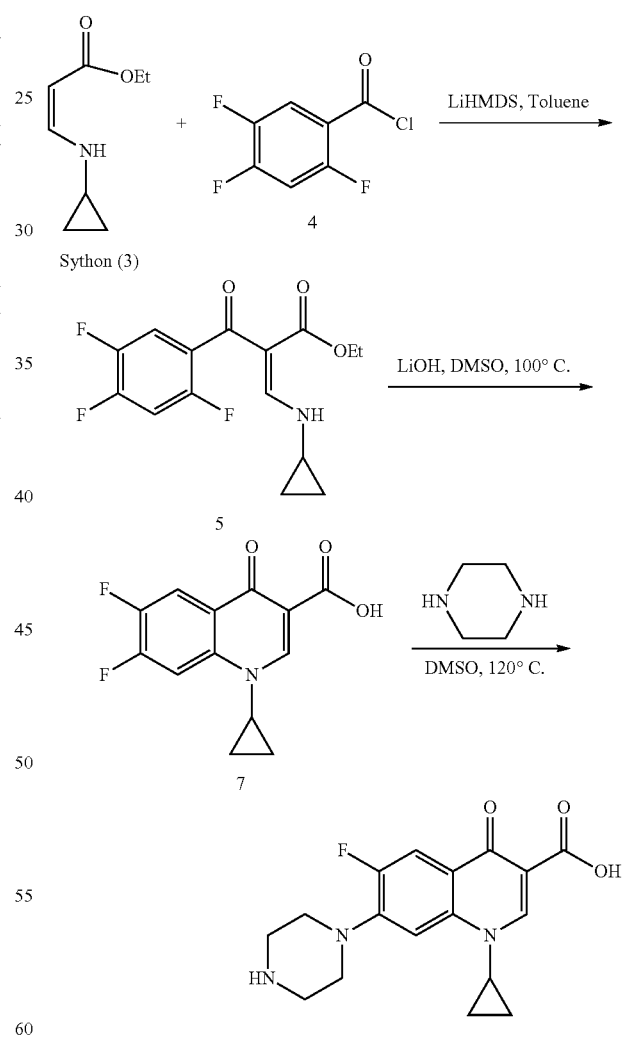

Synthesis Route 2 assumes a source of Synthon 3 and begins with the reaction between synthon 3 and reactant 4 (as in Synthesis Route 1) in suitable solvents such as but not limited to a combination of LiHMDS and toluene (PhMe) or tetrahydrofuran (THF), as described above for Synthesis Route 1, to yield intermediate 5

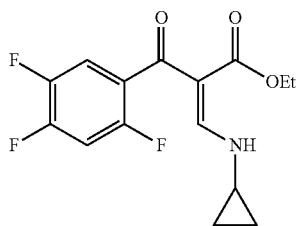

5

Thereafter, the Synthesis Routes 1 and 2 diverge. In Synthesis Route 2,5 is reacted with e.g. LiOH in a suitable solvent such as DMSO (or DMF, NMP, ACN, H₂O, or combinations thereof) at a temperature in the range of about 60 to about 180° C., e.g. at about 60, 70, 80, 90, 100, 110, 120, 130, 140, 150, 160, 170, 180° C., such as at 100° C., to yield intermediate 7:

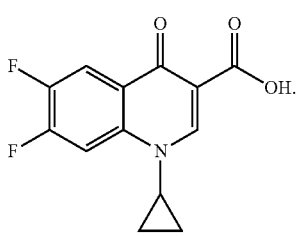

7

Intermediate 7 is converted to the final product, ciprofloxacin, by reaction with piperazine at temperature in the range of about 50 to about 150° C., e.g. at about 50, 60, 70, 80, 90, 100, 110, 120, 130, 140 or 150° C., such as at 100° C., to yield intermediate 1. The drug is recovered (purified, isolated, etc.) using methods described elsewhere herein and/or by other methods known in the art.

Exemplary Ciprofloxicin Synthesis Routes 3 and 4

Synthesis Routes 3 and 4 both proceed by assuming a source of Synthon 3 and reacting Synthon 3 and compound 4 to produced intermediate 6

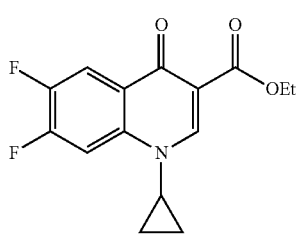

6 which is then converted directly to the final product, ciprofloxacin. However, the reaction conditions differ for the two routes.

Exemplary Ciprofloxicin Synthesis Route 3

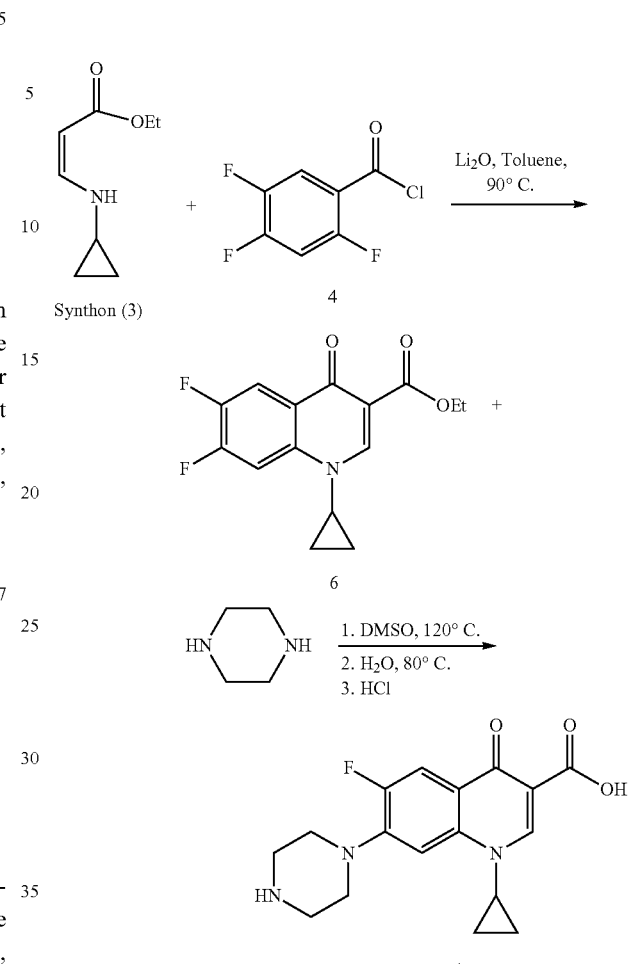

For Synthesis Route 3, Synthon 3 is reacted with compound 4 in the presence of Li₂O in toluene (or tetrahydrofuran) at a temperature in the range of 60 to 110° C., e.g. at 60, 65, 70, 75, 80, 85, 90, 95, 100, 105 or 110° C., such as at 90° C., to afford intermediate 6. Intermediate 6 is reacted with piperazine in, for example, DMSO (or in some aspects in DMF, NMP, ACN, or other suitable solvent). Addition of water to generate LiOH in situ affords the de-esterified intermediate 9 to afford the final product (1), which is then purified using methods described elsewhere herein and/or by other methods known in the art to yield the final product, ciprofloxacin.

Exemplary Ciprofloxicin Synthesis Route 4

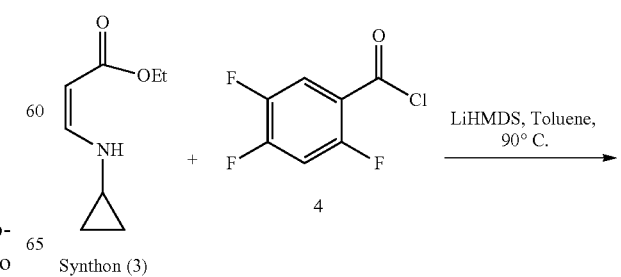

19
-continued

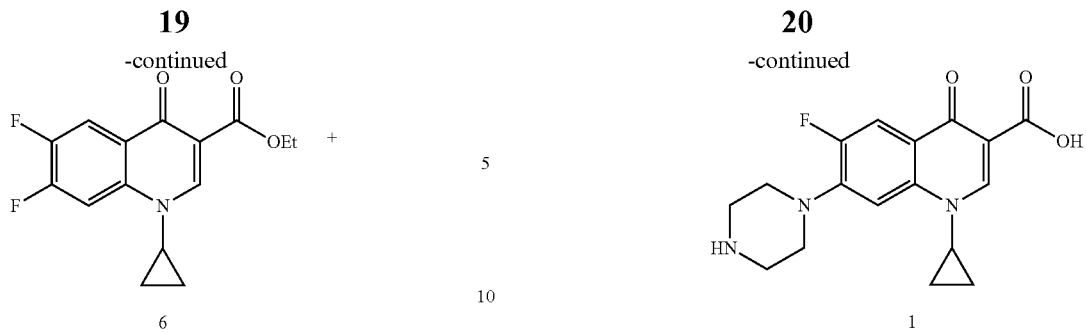

20
-continued

In contrast to Synthesis Route 3, in Synthesis Route 4, Synthon 3 and compound 4 are reacted in the presence of LiHMDS in toluene (or in another suitable solvent) at a temperature from about −78° C. to room temperature to yield intermediate 6 in a quantitative yield. Also in contrast to Synthesis Route 3, reaction of intermediate 6 with piperazine is performed at a temperature in the range of 80 to 100° C., e.g. at 80, 85, 90, 95 or 100° C., such as at 90° C., in a solvent such as DMSO (or DMF, NMP, ACN). For this reaction, NaOH (or LiOH, or excess LiHMDS from step 1) is used to for the de-esterification of intermediate 9. The reaction proceeds for approximately 2 to 3 hours to yield the final product, ciprofloxacin (1).

Continuous Flow Process: Exemplary Ciprofloxicin Synthesis Route 5

In addition, the present disclosure provides continuous flow processes which require fewer (e.g. only three) reactors and unit operations compared to the prior art.

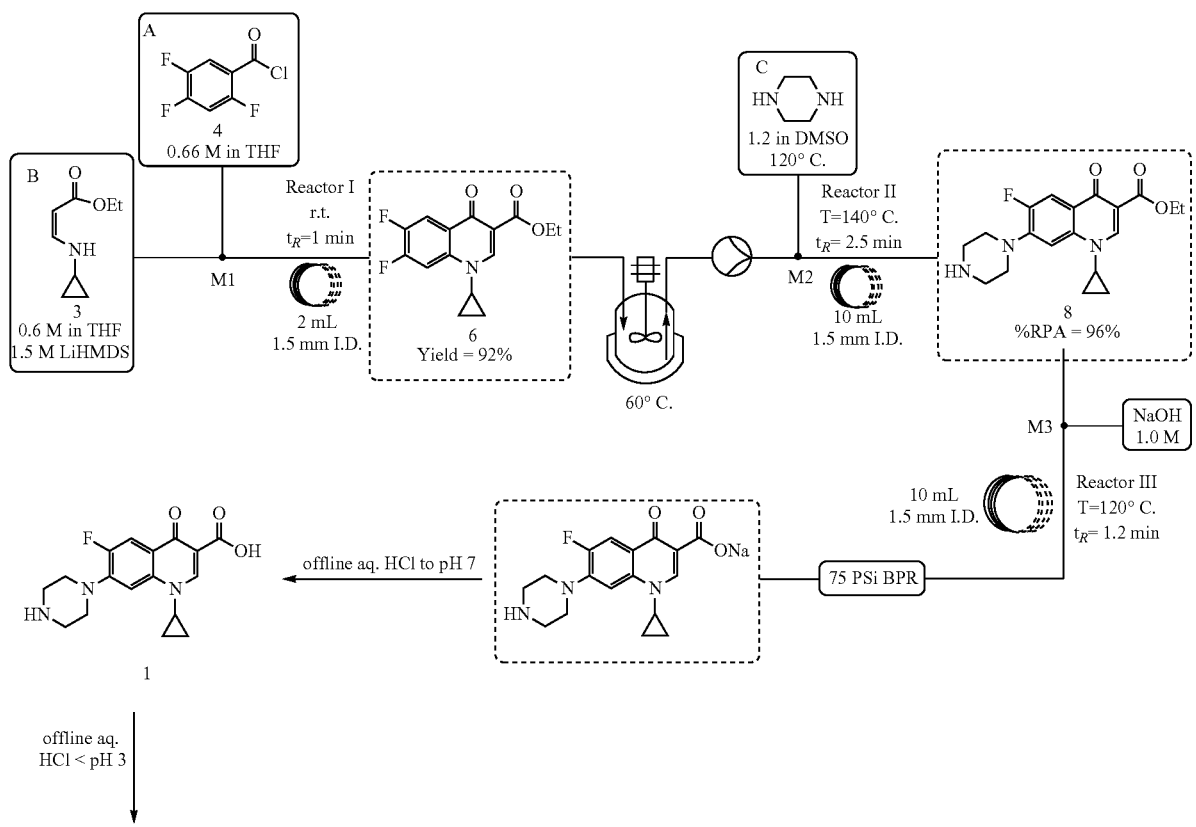

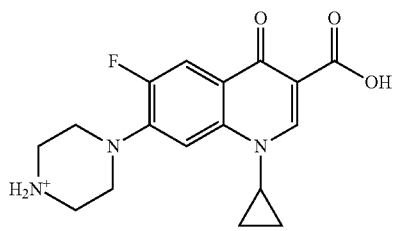

Ciprofloxacin Hydrochloride

In an exemplary synthesis, the first step is performed in a first reactor, where Synthon 3 and compound 4 (shown below) are mixed in a ratio of from about 1 equiv to about 1.1 equiv in the presence of a lithiating agent in a suitable solvent such as toluene or tetrahydrofuran (THF). For example, a solution of Synthon 3 (0.6M) and 1.5 M LiHMDS and a solution of compound 4 (0.66M) in THF are reacted.

4

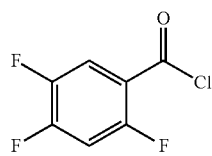

The reaction takes place e.g. at a temperature of from about −78° C. to about 25° C., such as at room temperature, and requires only a few minutes (e.g. about 1 minute) to yield the product intermediate 6

6

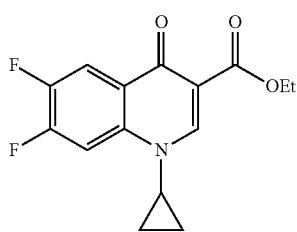

in a yield greater than about 80%, e.g. about 80, 85, 90, 91, 92, 93, 94 or 98% yield, such as about 94%.

In a second reactor (e.g. a heated batch reactor), Intermediate 6 is reacted with piperazine in a solvent such as DMSO, DMF, NMP or ACN, and heated at an elevated temperature in the range of from about 130 to 150° C., e.g. about 130, 135, 140, 145 or 150° C. In some aspects, 1.2 M DMSO is used. The reaction is completed in reactor II in approximately 1-5 minutes, such as e.g. 1.5, 2.0, 2.5, 3.0, 3.5, 4.0, 4.5 or 5.0 minutes. The resulting product is Intermediate 8

8

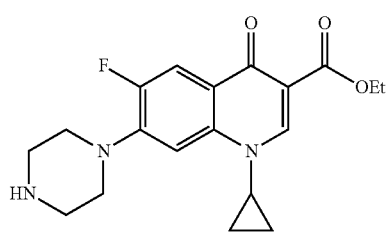

The next step of the synthesis routes takes place in a third reactor. In the third reactor, Intermediate 8 is combined with a strong base (such as 1.0M NaOH or LiOH) and reacted under a pressure ranging from about 40 to about 100 PSI, e.g. about 40, 45, 50, 55, 60, 65, 70, 75, 80, 85, 90, 95, 100 PSI. In some aspects, the pressure is 40 PSI or 75 PSI.

The product that results is

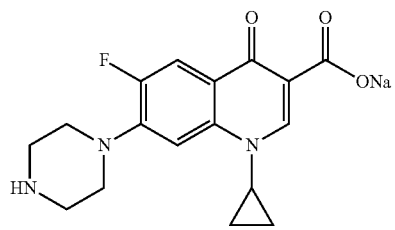

which is converted to ciprofloxacin offline by adjusting the pH to near neutrality (e.g. to about pH 7) e.g. using a strong acid such as HCl.

If needed, the ciprofloxacin may be further converted to ciprofloxacin hydrochloride by further lowering the pH, e.g. to about 3 or less.

Synthesis of Additional Fluoroquinolines

While in some aspects the technology described herein is used for the synthesis of ciprofloxacin, the reaction steps and/or the reactants that are used can be modified or substituted so that other compounds of interest are synthesized. For example, in some aspects, the amine piperazine is replaced by a compound such as but not limited to: 2-methylpiperazine, pyrrolidin-3-amine, (3aS,6aS)-octahydropyrrolo[3,4-b]pyrrole, etc.

Examples of such syntheses include but are not limited to:

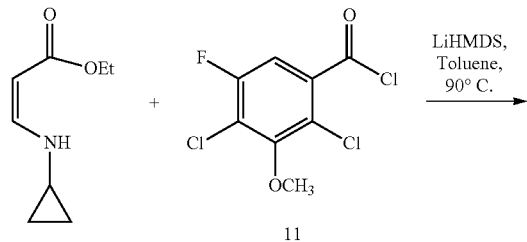

Synthon (3)

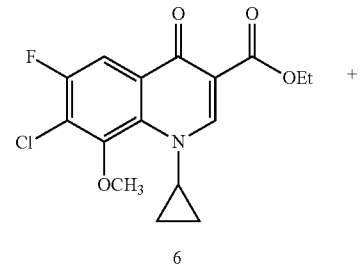

6

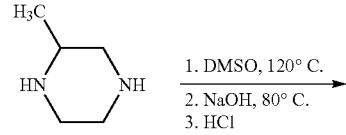

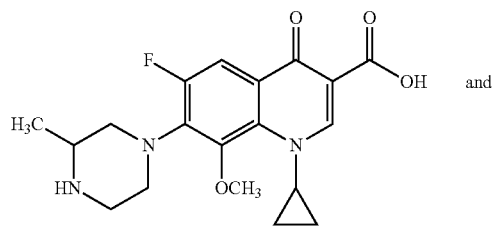

12 (Gatifloxacin)

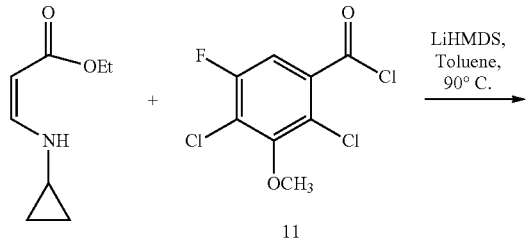

Synthon (3)

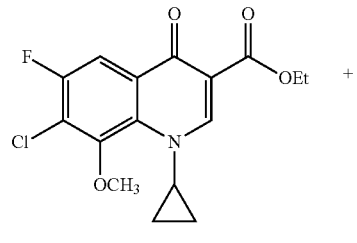

6

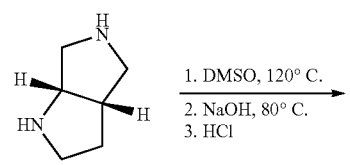

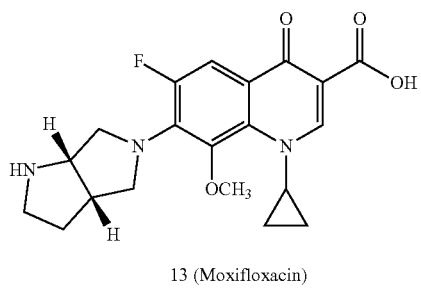 [SMILES: COc1c(N2C[C@@H]3CCN[C@@H]3C2)c(F)cc2c(=O)c(C(=O)O)cn(C3CC3)c12]

13 (Moxifloxacin)

The reaction conditions depicted are representative and can be varied e.g. by using different temperatures, alternative solvents, etc. as discussed above for ciprofloxacin. Other fluoroquinolines (including but are not limited to: grepafloxacin, sparfloxacin and cinafloxacin) can be synthesized in a similar manner by varying the identity of

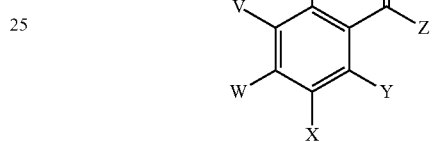

and/or the compound that contains a reactive amine, as shown in Table A:

TABLE A

| Fluoroquinolone | | Compound with reactive amine |
|---|---|---|
| Grepafloxacin | (structure with CH$_3$, F, Cl, Cl, acyl chloride) | (3-methylpiperazine) |
| Sparfloxacin | (structure with NH$_2$, F, F, F, acyl chloride) | (3,5-dimethylpiperazine) |
| Cinafloxacin | (structure with F, Cl, Cl, Cl, acyl chloride) | (3-aminopyrrolidine) |

TABLE A-continued

| Fluoroquinolone | | Compound with reactive amine |
|---|---|---|
| Besifloxacin | | |
| Enoxacin | | |
| Pefloxacin | | |
| Norfloxacin | | |

Formulations

Fluoroquinolone formulations for storage and/or for use as a medicament (e.g. for administration to a subject in need thereof, such as a subject with an infection) are known in the art. For example, ciprofloxacin may be prepared for administration in any suitable form, e.g. forms described in published US patent applications 20180092912, 20170035753, 20160000948, 20110150983 and 20070049552, the complete contents of each of which is hereby incorporated by reference. The fluoroquinolone compositions may be solids, liquids, semisolids, etc. in the form of pills, syrups, powders, freeze-dried forms, reconstitutable forms, etc. The fluoroquinolones can be prepared and used for administration, for example, by mouth (in solid or liquid form), in eye or ear drops, topically, for inhalation, intravenously, etc.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. Synthesis of Synthon 3

The routes of synthesizing ciprofloxacin described herein take advantage of an early stage insertion of the cyclopropyl amine moiety to afford the synthon 3. Batch reaction conditions for this high yielding amine insertion step are shown in Table 1. Such reactions also provided the potential to readily access structurally diverse N-substituted ciprofloxacin analogues.

TABLE 1

Synthesis of enamines from vinyl ethers[a]

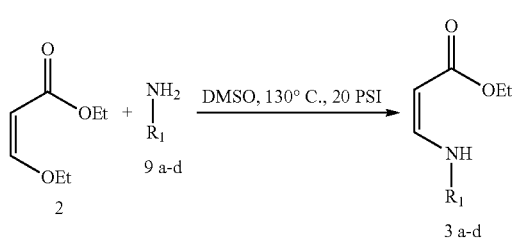

TABLE 1-continued

| Compound | R[1] | Conv (%)[b] to 12a-d | Product (%) |
|---|---|---|---|
| 9-a | cyclopropyl | 100 | 3-a (98) |
| 9-b | propyl | 96 | 3-b (94) |
| 9-c | benzyl | 89 | 3-c (85) |
| 9-d | cyclohexyl | 91 | 3-d (87.3) |

[a]Reaction conditions: 2 (1.0 equiv), 9a-d (3.0 equiv), DMSO. All reactions were carried out at 130° C., at 25 PSI under argon.
[b]Conversions are determined by HPLC.

With 3a in hand, we set out to identify reaction conditions that would afford the acylation of the benzoyl chloride to vinylogous amine. A recent attempt to achieve the C-acylation resulted in a mixture of N-acylation and C-acylation when weak bases are used in a ratio of 6:1 under the best conditions (Lin, et al. *Angew. Chemie—Int. Ed.* 2017, 8870-8873). Moreover, when 3 was deprotonated with BuLi followed by acylation with 4, a mixture of the acylation and a precipitate of the cyclization product was obtained.

Consistent with previous reports, the attempt to acylate 3 to 4 in the presence of weak bases required high temperature, longer reaction time and afforded a mixture of the C-acylation (5) and predominantly the N-acylation (10) products (Table 2). In contrast, lithiation of the enamine 3 by treating it with LiHMDS followed by reaction with the benzoyl chloride afforded the desired product 5 with a 96% yield with no evidence of N-acylation (entry 5 in Table 2).

TABLE 2

C-acylation optimization[a]

| Entry | Base | Temp (° C.) | 13a:13b ratio | Conv. (%)[b] |
|---|---|---|---|---|
| 1 | Et₃N | 90 | 1:7 | 10.5 |
| 2 | Pyridine | rt | 1:13 | 5 |
| 3 | DBU | 90 | 1:10 | 6 |
| 4 | DIPEA | 90 | 1:10 | 6 |
| 5* | LiHMDS | rt | >100:1 | 100 (96%)[c] |
| 7 | NaH | 0 | 1:60 | 2 |

[a]Reaction conditions: 3 (1.0 equiv), 2,4,5-trifluorobenzoyl chloride (1.2 equiv), base (1.2 equiv), toluene.
[b]Conversion was determined by HPLC.
[c]Isolated yield.

Consistent with previous reports, 5 cyclizes in a the presence of 3 equivalents of strong bases (Table 3, entries 1-4). When 5 was treated with LiHMDS, 6 was prepared with a quantitative yield (Table 3, entry 5).

TABLE 3

One step synthesis of compound 6[a]

| Entry | Base | Temp (° C.) | Solvent | Conv (%)[b] |
|---|---|---|---|---|
| 1 | DBU | 90 | DMSO | 98 |
| 2 | K₂CO₃ | 90 | DMSO | 98 |
| 3 | NaH | 90 | DMSO | 96 |
| 4 | LiOH | 90 | DMSO | 98 (acid) |
| 5 | LiHMDS | rt | Toluene | 98 (95[c]) |

[a]Reaction conditions: 5 (1.0 equiv), base (1-4) (3 equiv). LiHMDS (1.1 equiv)
[b]Conversion are determined by HPLC.
[c]Isolated yield.

We then evaluated the consolidation of the acylation and the ring closure in one step. 4 and 3 were treated with the stoichiometry of LiHMDS increased to 2.5, with a slow warming to room temperature, to afford 6 at a quantitative yield (scheme 1).

Scheme 1. Telescoped synthesis of 1. [a]Reaction conditions: 3 (1.0 equiv), 4 (1.1 equiv). LiHMDS (2.5 equiv), -78° C. to r.t., 2 hrs; piperazine (4 equiv), H₂O, 90° C., NaOH (4 equiv).

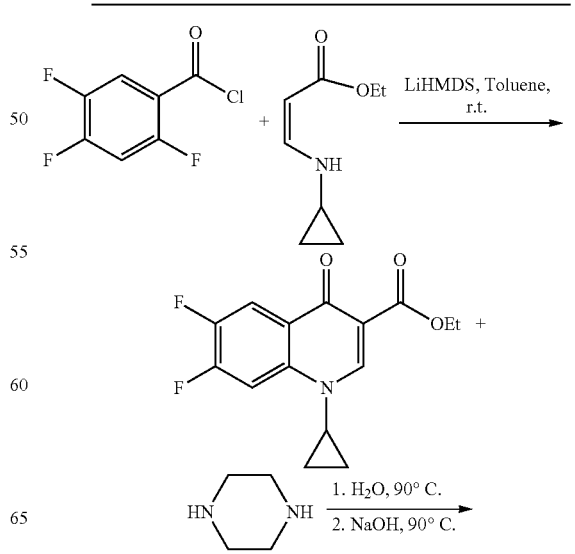

-continued

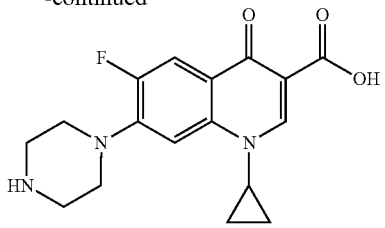

The piperazine coupling proceeded at high temperature to afford 8 in a 92% yield both in H₂O and DMSO as solvent. A hydrolysis of the ester afforded ciprofloxacin (scheme 1).

For the continuous preparation of ciprofloxacin, we envisioned a telescoped process over three reactors. In the most recent report, 1 was prepared on a continuous flow platform over five reactors and over 9 mins (Lin, et al. *Angew. Chemie—Int. Ed.* 2017, 8870-8873). We envisioned to design a scalable process, with shorter residence times and reduced unit operations for a continuous flow synthesis of 1. The streamlined continuous preparation of ciprofloxacin began with streaming the lithiated 3 and 4 over a 2 mL reactor coil. The transformation was achieved in 1 min in a 92% yield. The synthesis of 6 over the reactor coil resulted in clogging when toluene was used. THF appears to be the best solvent for this step.

We have observed that a heating of 6 and the piperazine are required to avoid the clogging of the reactor II. Hence, we introduce a heating stage by streaming the outlet from reactor I into a heated batch reactor. The inlet from the heated reactor is allowed to mix with the heated piperazine in the reactor II at 140° C., under 75 PSI. The reaction proceeded yielding a 95% conversion to 8 in 2.5 min. Subsequently, the hydrolysis of 8 proceeded at 120° C. in reactor III to afford 1.

Scheme 2. Continuous flow synthesis of ciprofloxacin (1)
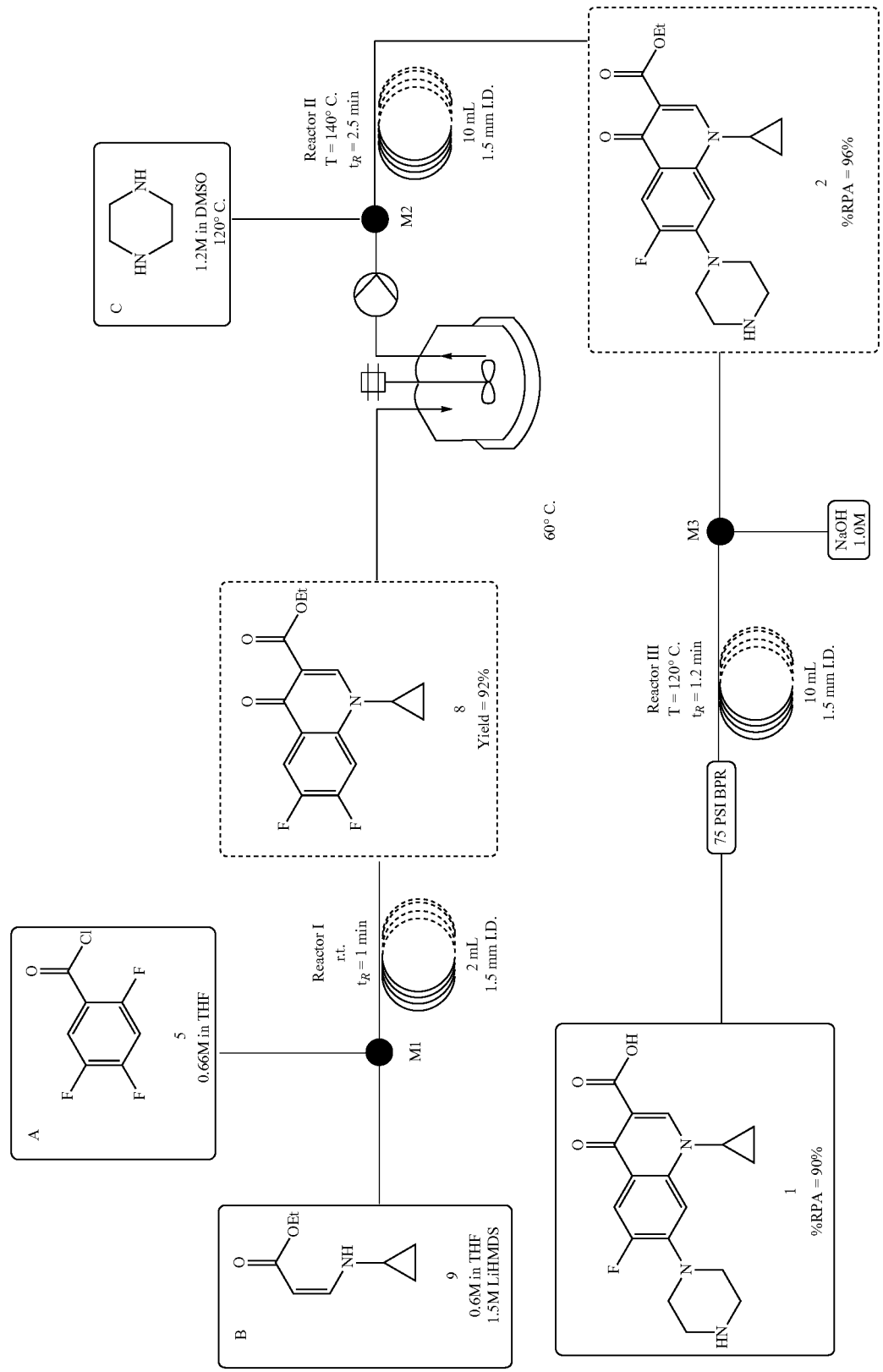

Experimental for Examples 1 and 2

All reagents and solvents were used as received without further purification. Microwave reactions were carried out in a Biotage Initiator. Continuous flow experiments were carried out using an E-series flow reactor instrument purchased from Vapourtec Ltd. PFA tubing (1/16 OD×1 mm ID) was used for all reactor coils in flow experiments. $^1$H and $^{13}$C were recorded in CDCl$_3$ (600 and 125 MHz, respectively) on a Bruker FT-NMR spectrometer. NMR data were processed using a MestReNova 10.0 software package. Chemical shift (δ) values are reported in parts per million (ppm) relative to TMS and coupling constants (J) are reported in Hz. Known products were characterized by comparison to the corresponding 1H NMR and 13C NMR from literature. The names of the products were generated using PerkinElmer ChemBiodraw Ultra v.12.0.2 software package. All HPLC chromatograms were recorded on an Agilent Technologies 1260 Infinity instrument with a Poroshell 120 EC-C18 column (4.6×50 mm, 2.7 micron). All isolations of intermediates were performed for analytical purposes; otherwise the reaction were carried out in one pot to afford the final product.

General Procedure for the Amino Acrylate Reactions with the Vinyl Ether

To a solution of ethyl 3-ethoxyacrylate (5 g, 34.72 mmol) dissolved in DMSO (30 mL) in a 250-mL round-bottom pressure flask was added the appropriate amine. The vessel was heated to 130° C. and pressurized to 25 PSI under argon for 6 hrs. After cooling to room temperature, the reaction mixture was diluted in ethyl acetate (30 mL) and washed with water (2×10-mL), brine (10 mL) and dried over sodium sulfate. The filtrate was concentrated under pressure to afford the desired product. The purity was determined by HPLC and NMR, which showed the following:

Ethyl(Z)-3-(cyclopropylamino)acrylate (3)

$^1$H NMR (600 MHz, CDCl$_3$, 25° C.): δ 3.0 (s, 1H), 3.95 (br s, 4H), 6.75 (m, 1H), 6.87 (m, 1H), 7.61 (m, 1H); $^{13}$C NMR (125 MHz, CDCl$_3$): δ 50.0, 75.0, 104.4, 111.7, 123.0, 130.4, 158.5, 162.5. Purity (96%)

Ethyl(Z)-3-(cyclopropylamino)-2(2,4,5 trifluorobenzoyl)acrylate (5)

To a solution of ethyl(Z)-3-(cyclohexylamino)acrylate (5 g, 6.623 mmol) dissolved in toluene (8-mL) in a 250 mL three neck round bottom flask was slowly added lithium bis(trimethylsilyl)amide (9.95 mL, 9.95 mmol) at 0° C. under argon protection. The reaction mixture was stirred for 30 min following the dropwise addition of 2,4,5-trifluorobenzoyl chloride (1.42 g, 7.29 mmol). The reaction mixture was allowed to warm to room temperature and monitored for completion with HPLC. After completion, the reaction was quenched with ammonium chloride (20 mL), diluted in H$_2$O (25-mL) and extracted (3×25 mL) with dichloromethane. The reaction mixture was washed with brine (15 mL). The combined organic phases were dried over Na$_2$SO$_4$, filtered and concentrated. The residue was purified by flash column chromatography (3:1 hexanes/ethyl acetate) to afford (5).

Ethyl(Z)-3-(benzylamino)acrylate

To a solution of ethyl 3-ethoxyacrylate (5 g, 34.72 mmol) dissolved in DMSO (30 mL) in a 250 mL round-bottom pressure flask was added benzylamine (11.16 g, 104.10 mmol). The vessel was pressurized to 20 PSI and stirred at 130° C. for 6 hrs. After cooling to room temperature, the reaction mixture was diluted in dichloromethane (30 mL) and washed with water (2×10 mL), brine (10 mL) and dried over sodium sulfate. The filtrate was concentrated under pressure to afford ethyl(Z)-3-(benzylamino)acrylate—6.10 g (85.1%) purity by HPLC 90.4%. 4.31 min By-Product peak 3% 3.38 min and 6.6% 5.08 min [ACN 5-95 11 min].

Ethyl(Z)-3-(propylamino)acrylate

To a solution of ethyl 3-ethoxyacrylate (5 g, 34.72 mmol) dissolved in DMSO (30 mL) in a 250 mL round-bottom pressure flask was added propylamine (6.15 g, 104.10 mmol). The vessel was pressurized to 25 PSI and stirred at 130° C. for 4 hrs. After cooling to room temperature, the reaction mixture was diluted in dichloromethane (30 mL) and washed with water (2×10 mL), brine (10 mL) and dried over sodium sulfate. The filtrate was concentrated under pressure to afford ethyl(Z)-3-(propylamino)acrylate—5.01 g (93.1%) purity by HPLC 94.1%. 3.71 min by-Product peak 5.9% 4.54 min [ACN 5-95 11 min].

Example 2. Further Synthesis Reactions

Microwave synthesis of Ethyl(Z)-3-(cyclopropylamino)acrylate (3)

7.64 mmoles of ethyl(Z)-3-ethoxyacrylate was added to 30.55 mmoles of cyclopropylamine in 0.5 mL of DMF. The mixture was irradiated by microwave at 150° C. for 1 h. After completion of the reaction as indicated by HPLC, the reaction mixture was dissolved in 10 mL of water and extracted with dichloromethane (3×25 mL), followed by washing with brine (10 mL) and dried over sodium sulfate. The solvent was removed under pressure to yield the product as a yellow oil (1.14 g, 96%).

NMR (600 MHz, CDCl$_3$): δ 3.0 (s, 1H), 3.95 (br s, 4H), 6.75 (m, 1H). 6.87 (m, 1H), 7.61 (m, 1H);
$^{13}$C NMR (125 MHz, CDCl$_3$): δ 50.0, 75.0, 104.4, 111.7, 123.0, 130.4, 158.5, 162.5.

Batch Synthesis of Ethyl(Z)-3-(cyclopropylamino)acrylate (3)

To a solution of ethyl 3-ethoxyacrylate (0.104 mmol) dissolved in DMSO (60 mL) in a 250-mL round-bottom pressure flask was added cyclopropylamine (0.416 mmol). The vessel was heated to 130° C. and pressurized to 25 PSI under argon for 6 hrs. After cooling to room temperature, the reaction mixture was diluted in ethyl acetate (30 mL) and washed with water (2×10-mL), brine (10 mL) and dried over sodium sulfate. The filtrate was concentrated under pressure to afford the desired product (15.5 g, 96%).

$^1$H NMR (600 MHz, CDCl$_3$): δ 3.0 (s, 1H), 3.95 (br s, 4H), 6.75 (m, 1H), 6.87 (m, 1H), 7.61 (m, 1H);
$^{13}$C NMR (125 MHz, CDCl$_3$): δ 50.0, 75.0, 104.4, 111.7, 123.0, 130.4, 158.5, 162.5.

Synthesis Route 1

Ethyl(Z)-3-(cyclopropylamino)-2-(2,4,5-trifluorobenzoyl)acrylate (5)

A three necked, dried round bottom flask equipped with a stirring bar and under argon was charged with lithium bis(trimethylsilyl)amide (6.07 mL, 6.07 mmoles in toluene) and cooled to −78° C. followed by a slow addition of the acrylate (3) (5.05 mmoles). The resulting bright yellow solution was stirred for 30 mins followed by the dropwise addition of 2,4-dichloro-5-fluorobenzoyl chloride (6.07 mmoles). The mixture was allowed to warm to room temperature and stirred for 1 h. After the completion of the reaction, the reaction mixture was quenched with saturated aqueous $NH_4Cl$ (10 mL). The organic layer was washed with brine and dried over $Na_2SO_4$. The organic solvent was removed under pressure. The crude mixture was purified by flash chromatography on a silica gel column using a mixture of hexanes/EtOAc as eluent resulting in a yellowish powder (1.5 g, 96%).

Ethyl 1-cyclopropyl-6,7-difluoro-4-oxo-1,4-dihydro-quinoline-3-carboxylate (6)

To a solution of 5 (3.19 mmoles) in DMSO (20 mL) in a round bottom flask was added DBU (12.77 mmoles) and the mixture was heated to 90° C. The reaction was monitored by HPLC. Upon complete consumption of the starting material, the reaction mixture was cooled to room temperature, diluted in water (25 mL), extracted with dichloromethane (3×25 mL), washed with brine (25 mL) and dried over $Na_2SO_4$. The filtrate was concentrated under pressure and purified by flash chromatography on a silica gel column using a mixture of hexanes/EtOAc as eluent to afford the product (0.86 g, 92%).

Ethyl 1-cyclopropyl-6-fluoro-4-oxo-7-(piperazin-1-yl)-1,4-dihydroquinoline-3-carboxylate (8)

To a solution of 6 (3.41 mmoles) in DMSO (20 mL) in a round bottom flask was added the piperazine (13.65 mmoles) and the mixture was heated to 90° C. The reaction was monitored so by HPLC. Upon complete consumption of the starting material, the reaction mixture was cooled to room temperature, diluted in water (25 mL), extracted with dichloromethane (3×25 mL), washed with brine (25 mL) and dried over $Na_2SO_4$. The filtrate was concentrated under pressure and purified by flash chromatography on a silica gel column using a mixture of DCM/MeOH as eluent to afford the product (1.1 g, 90%).

1-cyclopropyl-6-fluoro-4-oxo-7-(piperazin-1-yl)-1,4-dihydroquinoline-3-carboxylic acid (1)

To a solution of 8 (2.78 mmoles) in DMSO (10 mL) in a round bottom flask was added NaOH (12 mmoles) and the mixture was heated to 90° C. The reaction was monitored by HPLC. Upon complete consumption of the starting material, the reaction mixture was cooled to room temperature. 4 N HCl was added to the mixture to adjust the pH to 7. Ciprofloxacin (1) was allowed to gradually precipitate in a 4° C. fridge. The solid was filtered, washed three times with water and three times with acetone and dried, affording 717 mg yellow solid.

Synthesis Route 2

Ethyl(Z)-3-(cyclopropylamino)-2-(2,4,5-trifluorobenzoyl)acrylate (5)

A three necked, dried round bottom flask equipped with a stirring bar and under argon was charged with lithium bis(trimethylsilyl)amide (6.07 mL, 6.07 mmoles in toluene) and cooled to −78° C. followed by a slow addition of the acrylate (3) (5.05 mmoles). The resulting bright yellow solution was stirred for 30 mins followed by the dropwise addition of 2,4-dichloro-5-fluorobenzoyl chloride (6.07 mmoles). The mixture was allowed to warm to room temperature and stirred for 1 h. After the completion of the reaction, the reaction mixture was quenched with saturated aqueous $NH_4Cl$ (10 mL). The organic layer was washed with brine and dried over $Na_2SO_4$. The organic solvent was removed under pressure. The crude mixture was purified by flash chromatography on a silica gel column using a mixture of hexanes/EtOAc as eluent resulting in a yellowish powder (1.5 g, 96%).

1-cyclopropyl-6,7-difluoro-4-oxo-1,4-dihydroquinoline-3-carboxylic acid (7)

To a solution of 5 (2.89 mmoles) in DMSO (30 mL) was added LiOH (8.67 mmoles) and the mixture was heated to 120° C. After complete consumption of the starting material, the reaction mixture was cooled to room temperature, diluted in ethyl acetate (75 mL) washed with water (3×25), brine (25 mL) and dried over $Na_2SO_4$. The filtrate was concentrated under pressure to afford the product (704 mg, 92%).

1-cyclopropyl-6-fluoro-4-oxo-7-(piperazin-1-yl)-1,4-dihydroquinoline-3-carboxylic acid (1)

To a solution of 7 (3.77 mmoles) in DMSO (30 mL) in a round bottom flask was added the piperazine (15 mmoles) and the mixture was heated to 90° C. The reaction was monitored by HPLC. Upon complete consumption of the starting material, the reaction mixture was cooled to room temperature. 4 N HCl was added to the mixture to adjust the pH to 7. Ciprofloxacin (1) was allowed to gradually precipitate in a 4° C. fridge. The solid was filtered, washed three times with water and three times with acetone and dried, affording 960 mg yellow solid.

Synthesis Route 3

Ethyl(Z)-3-(cyclopropylamino)-2-(2,4,5-trifluorobenzoyl)acrylate (7)

A three necked, dried round bottom flask equipped with a stirring bar and under argon was charged with lithium oxide (51.6 mmoles) in toluene followed by a slow addition of the acrylate (3) (12.9 mmoles). The reaction mixture was heated to 90° C. The resulting bright yellow solution was stirred for 30 mins followed by the dropwise addition of 2,4-dichloro-5-fluorobenzoyl chloride (15.48 mmoles). After the complete consumption of 3, the reaction mixture was cooled to room temperature and quenched with saturated aqueous 1 N HCl to adjust the pH to 4. The crude mixture was diluted in water and the organic layer was extracted with dichloromethane (3×25), washed with brine (25 mL) and dried over $Na_2SO_4$. The filtrate was concentrated under pressure and purified by flash chromatography on a silica gel column using a mixture of hexanes/EtOAc as eluent to afford the product (3.2 g, 93%).

Ciprofloxacin

To a solution of 7 (11.32 mmoles) in DMSO (60 mL) in a round bottom flask was added piperazine (45.3 mmoles) and the mixture was heated to 90° C. The reaction was monitored by HPLC. Upon complete consumption of the starting material, 10 mL of $H_2O$ was slowly added and the reaction was stirred until complete conversion to 1. The reaction mixture was cooled to room temperature. 4 N HCl was added to the mixture to adjust the pH to 7. Ciprofloxacin (1) was allowed to gradually precipitate in a 4° C. fridge. The solid was filtered, washed three times with water and three times with acetone and dried, affording 2.8 g yellow solid.

Synthesis Route 4

Ethyl(Z)-3-(cyclopropylamino)-2-(2,4,5-trifluorobenzoyl)acrylate (6)

A three necked, dried round bottom flask equipped with a stirring bar and 70 mL of toluene under argon was charged with lithium bis(trimethylsilyl)amide (32.25 mmoles in toluene) and cooled to −78° C. followed by a slow addition of the acrylate (3) (12.9 mmoles). The resulting bright yellow solution was stirred for 30 mins followed by the dropwise addition of 2,4-dichloro-5-fluorobenzoyl chloride (15.48 mmoles). The mixture was allowed to warm to room temperature and stirred for 1 h. Upon complete consumption of the starting material, the reaction mixture was cooled to room temperature, quenched with saturated aqueous $NH_4Cl$ (10 mL), extracted with dichloromethane (3×25), washed with brine (25 mL) and dried over $Na_2SO_4$. The filtrate was concentrated under pressure and purified by flash chromatography on a silica gel column using a mixture of hexanes/EtOAc as eluent to afford the product (3.4 g).

1-cyclopropyl-6-fluoro-4-oxo-7-(piperazin-1-yl)-1,4-dihydroquinoline-3-carboxylic acid (1)

To a solution of 6 (10.23 mmoles) in DMSO (60 mL) in a round bottom flask was added piperazine (41 mmoles) and the mixture was heated to 90° C. The reaction was monitored by HPLC. Upon complete consumption of the starting material, 1M aqueous NaOH (8.67 mmoles) was added and the reaction was stirred for 2-3 h at 90° C. Upon completion of the reaction, the crude mixture was cooled to room temperature. 4 N HCl was added to the mixture to adjust the pH to 7. Ciprofloxacin (1) was allowed to gradually precipitate in a 4° C. fridge. The solid was filtered, washed three times with water and three times with acetone and dried, affording 2.53 g yellow solid.

Continuous Flow Synthesis

The sequence was run on two vaportek E-series units. Solutions A-B were prepared in oven-dried 25 mL screw cap volumetric flasks under an argon atmosphere. Without any precautions, solutions C-D were prepared in a 50 mL volumetric flask. Back pressure was regulated with a back pressure regulator (BPR). Mixing was done by combining two streams into a tee (IDEX Health & Science).

TABLE 3

Solution preparation list for the synthesis

| Solution Stream | Composition | Pump | Flow Rate (ml/min) |
|---|---|---|---|
| A | 5 (0.66M in THF) | A | 1 |
| B | 9 (0.06M in THF) LiHMDS (1.5M in THF) | B | 1 |
| C | Piperazine (1.2M in DMSO) | C | 2 |
| D | NaOH (1.0M in $H_2O$) | D | 4 |

The whole sequence was run as follows: before pumping, all reactors were primed with anhydrous THF. Solutions A and B were mixed into Reactor I (1.57 mm ID, 2.03 mm OD, 2 mL) at ambient temperature for a residence time of 1 min. The outlet stream was collected into a round bottom flask under an argon atmosphere and was continuously heated at 60° C. with vigorous stirring. The heated mixture was mixed with solution C (heated to 120° C.) and passed through coiled PFA Reactor II (1.57 mm ID, 2.03 mm OD, 10 mL) at 140° C. for a residence time of 2.5 min. The outlet stream was mixed with solution D and passed into Reactor III (1.57 mm ID, 2.03 mm OD, 10 mL) at 100° C. for a residence time of 1.2 min. The outlet stream was passed through a 75 psi BPR. The outlet stream was collected for 5 min after running the sequence for 14 min (3 residence times). The collected fraction was cooled to room temperature. 4 N HCl was added to the mixture to adjust the pH to 7. Ciprofloxacin (1) was allowed to gradually precipitate in a 4° C. fridge. The solid was filtered, washed three times with water and three times with acetone and dried to yield the yellowish solid.

REFERENCES

[1] K. P. Cole, M. D. Johnson, Expert Rev. *Clin. Pharmacol.* 2018, 11, 5-13.
[2] J. Verghese, C. J. Kong, D. Rivalti, E. C. Yu, R. Krack, J. Alcázar, J. B. Manley, D. T. McQuade, S. Ahmad, K. Belecki, et al., *Green Chem.* 2017, 19, 2986-2991.
[3] R. Dach, J. J. Song, F. Roschangar, W. Samstag, C. H. Senanayake, *Org. Process Res. Dev.* 2012, 16, 1697-1706.
[4] M. Goldbach, E. Danieli, J. Perlo, B. Kaptein, V. M. Litvinov, B. Blumich, F. Casanova, A. L. L. Duchateau, *Tetrahedron Lett.* 2016, 57, 122-125.
[5] H.-J. Federsel, *Acc. Chem. Res.* 2009, 42, 671-680.
[6] D. Ott, D. Kralisch, I. Denčić, V. Hessel, Y. Laribi, P. D. Perrichon, C. Berguerand, L. Kiwi-Minsker, P. Loeb, *Chem Sus Chem* 2014, 7, 3521-3533.
[7] S. Caron, N. M. Thomson, *J. Org. Chem.* 2015, 80, 2943-2958.
[8] E. Yu, H. P. R. Mangunuru, N. S. Telang, C. J. Kong, J. Verghese, S. E. Gilliland, S. Ahmad, R. N. Dominey, B. F. Gupton, *Beilstein J. Org. Chem.* 2018, 14, 583-592.
[9] S. Korwar, S. Amir, P. N. Tosso, B. K. Desai, C. J. Kong, S. Fadnis, N. S. Telang, S. Ahmad, T. D. Roper, B. F. Gupton, *European J. Org. Chem.* 2017, 2017, 6495-6498.
[10] C. J. Kong, D. Fisher, B. K. Desai, Y. Yang, S. Ahmad, K. Belecki, B. F. Gupton, *Bioorg. Med. Chem.* 2017, DOI 10.1016/j.bmc.2017.07.004.
[11] R. Porta, M. Benaglia, A. Puglisi, *Org. Process Res. Dev.* 2016, 20, 2-25.
[12] M. Baumann, I. R. Baxendale, *Beilstein J. Org. Chem.* 2015, 11, 1194-1219.
[13] J. Britton, C. L. Raston, *Chem Soc Rev* 2017, 46, 1250-1271.
[14] A. Adamo, R. L. Beingessner, M. Behnam, J. Chen, T. F. Jamison, K. F. Jensen, J. C. Monbaliu, A. S. Myerson, E. M. Revalor, D. R. Snead, et al., *Science* (80-.). 2016, 352, 61-67.
[15] K. P. Cole, J. M. Groh, M. D. Johnson, C. L. Burcham, B. M. Campbell, W. D. Diseroad, M. R. Heller, J. R. Howell, N. J. Kallman, T. M. Koenig, et al., *Science* (80-.). 2017, 356, 1144-1150.
[16] H. Lin, C. Dai, T. F. Jamison, K. F. Jensen, *Angew. Chemie—Int. Ed.* 2017, 8870-8873.
[17] J. L. Howard, C. Schotten, D. L. Browne, *React. Chem. Eng.* 2017, 2, 61-67.

[18] B. Gutmann, D. Cantillo, C. O. Kappe, *Angew. Chemie—Int. Ed.* 2015, 54, 6688-6728.
[19] T. M. Braden, M. D. Johnson, M. E. Kopach, J. McClary Groh, R. D. Spencer, J. Lewis, M. R. Heller, J. P. Schafer, J. J. Adler, *Org. Process Res. Dev.* 2017, 21, 317-326.
[20] A. M. Emmerson, *J. Antimicrob. Chemother.* 2003, 51, 13-20.
[21] L. A. Mitscher, *Chem. Rev.* 2005, 105, 559-592.
[22] K. J. Aldred, R. J. Kerns, N. Osheroff, *Biochemistry* 2014, 53, 1565-1574.
[23] J. A. Linder, E. S. Huang, M. A. Steinman, R. Gonzales, R. S. Stafford, *Am. J. Med.* 2005, 118, 259-268.
[24] V. T. Andriole, 2005, 41, 113-119.
[25] G. Bartoli, C. Cimarelli, R. Dalpozzo, G. Palmieri, *Tetrahedron* 1995, 51, 8613-8622.
[26] C. H. Park, J. Lee, H. Y. Jung, M. J. Kim, S. H. Lim, H. T. Yeo, E. C. Choi, E. J. Yoon, K. W. Kim, J. H. Cha, et al., *Bioorganic Med. Chem.* 2007, 15, 6517-6526.
[27] G. Bartoli, G. Palmieri, M. Petrini, *Tetrahedron* 1990, 46, 1379-1384.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. A method of synthesizing ciprofloxacin, comprising
i) reacting

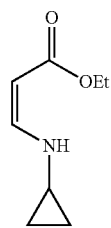 [SMILES: CCOC(=O)/C=C\NC1CC1]

with

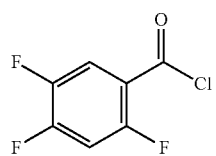 [SMILES: O=C(Cl)c1cc(F)c(F)cc1F]

to form

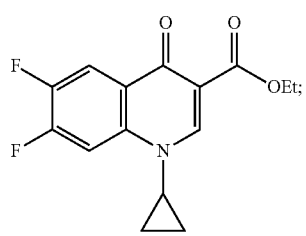 [SMILES: CCOC(=O)c1cn(C2CC2)c2cc(F)c(F)cc2c1=O]

ii) reacting

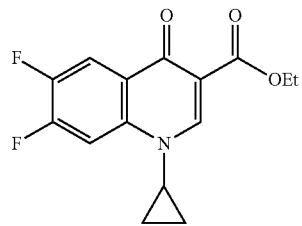 [SMILES: CCOC(=O)c1cn(C2CC2)c2cc(F)c(F)cc2c1=O]

with

to form

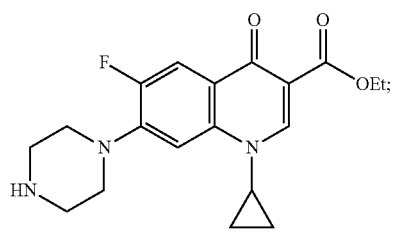 [SMILES: CCOC(=O)c1cn(C2CC2)c2cc(N3CCNCC3)c(F)cc2c1=O]

and iii) reacting

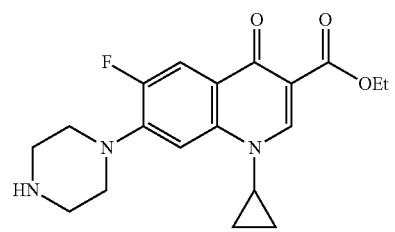 [SMILES: CCOC(=O)c1cn(C2CC2)c2cc(N3CCNCC3)c(F)cc2c1=O]

with a base to form ciprofloxacin:

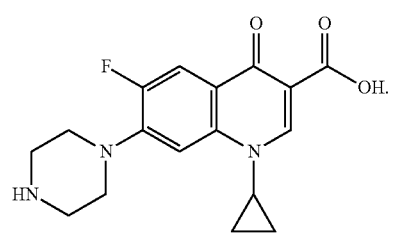

wherein

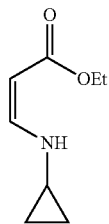 [SMILES: CCOC(=O)/C=C\NC1CC1]

is formed by reacting

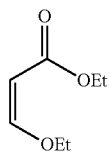

with

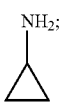

and wherein one or more of steps i)-iii) is performed using a microwave, a batch system or a flow reactor.

2. The method of claim 1, wherein one or more of steps i)-iii) is performed in a flow reactor.

3. The method of claim 1, wherein steps i)-iii) include:

i) in a first flow reactor, reacting

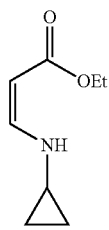 [SMILES: CCOC(=O)/C=C\NC1CC1]

with

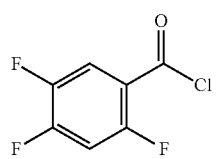 [SMILES: O=C(Cl)c1cc(F)c(F)cc1F]

at ambient temperature to yield

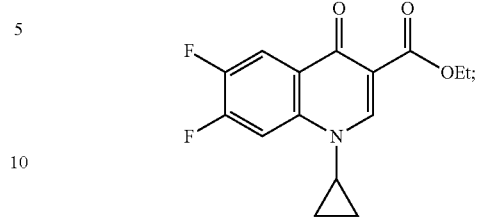

ii) in a second flow reactor, reacting the

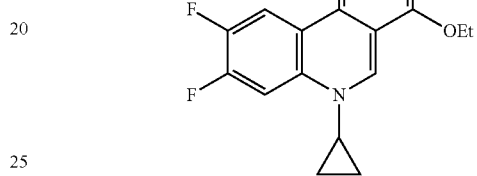

with piperazine

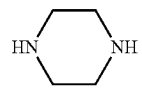

in the presence of dimethylsulfoxide (DMSO) and at a temperature in the range of 40° C. to 180° C. to yield

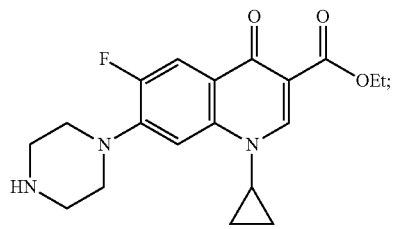 [SMILES: CCOC(=O)c1cn(C2CC2)c2cc(N3CCNCC3)c(F)cc2c1=O]

and iii) in a third flow reactor, reacting the

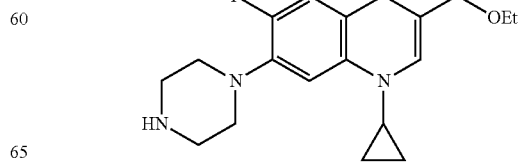

with a base, under pressure, to yield ciprofloxacin:
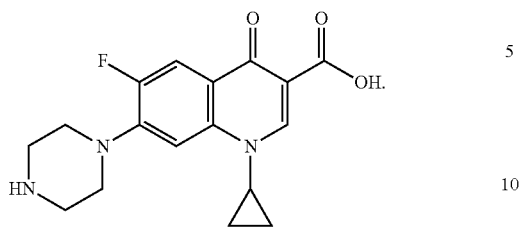
4. The method of claim 3 wherein the pressure in the third flow reactor is from 40 to 75 PSI.
5. The method of claim 3, wherein the base is 1.0 M NaOH.
* * * * *